United States Patent [19]
Paget

[11] 3,947,098
[45] Mar. 30, 1976

[54] LIGHT PROJECTOR DEVICE, PARTICULARLY FOR EYESIGHT EXAMINATION TESTS

[75] Inventor: Pierre Charles Paget, Ligny-en-Barrois, France

[73] Assignee: Essilor International "Compagnie Generale d'Optique", Joinville, France

[22] Filed: June 24, 1974

[21] Appl. No.: 482,566

[30] Foreign Application Priority Data
June 29, 1973 France .............................. 73.23859

[52] U.S. Cl. .................................. 351/30; 353/103
[51] Int. Cl.² ...................... A61B 3/02; G03B 23/10
[58] Field of Search ........................ 351/30; 353/103

[56] References Cited
UNITED STATES PATENTS
| | | | |
|---|---|---|---|
| 1,797,544 | 3/1931 | Cameron | 351/30 |
| 3,655,276 | 4/1972 | Wilkinson | 351/30 |

*Primary Examiner*—Paul A. Sacher
*Attorney, Agent, or Firm*—Young & Thompson

[57] ABSTRACT

A light projector device for projecting eyesight examination tests onto a screen comprises a test disc and a mask disc mounted one in front of the other with their peripheral regions in the path of a light beam from a light projection unit. The discs are rotatable by independent motors and the test disc has on its periphery a series of translucent areas carrying tests while the mask disc has a series of light passages capable of being superimposed on the test areas of the test disc in the light beam. A test carrier dial is adapted for rotation in the light beam about an axis co-axial with the optical axis of the projection unit, and this test carrier dial and the test disc are both mounted on a plate which is adapted to rock between two end positions. In one end position of the plate, the test disc is in engagement with drive means driven by the motor associated with the test disc, the periphery of the test disc is situated in the light beam and the test dial is situated at a distance from the beam, and in the other end position the test dial is engaged with the same drive means and is situated in the light beam, and the test disc is located at a distance from the beam. Thus a single motor is sufficient for the controlled independent rotation of both the test disc and the test dial.

18 Claims, 10 Drawing Figures

LIGHT PROJECTOR DEVICE, PARTICULARLY FOR EYESIGHT EXAMINATION TESTS

BACKGROUND OF THE INVENTION

The present invention relates to a light projector device for projecting tests on a screen. More particularly, the invention relates to a device for projecting eyesight examination tests, such as visual acuity and astigmatism tests.

The device is of the kind comprising two discs interposed successively in the light beam of a light projection unit, each of the said discs being mounted for rotation, under the control of a separate motor, about an axis situated at a distance from the axis of the light beam of the said projection unit, one of the discs, known as the test disc, carrying circularly on a ring a series of translucent areas carrying tests and the other, known as the mask disc, carrying a succession of light passages, such as apertures, transparent or other areas, capable of being individually superimposed on all or part of the test areas of the test disc in the said light beam, and a test carrier dial mounted for rotation separately and adapted to turn in the light beam of the projection unit about an axis which is substantially that of the said light beam, that is to say about an axis which is substantially the optical axis of the projection unit.

As a rule, when tests for the examination of sight are concerned, the tests carried by the translucent areas of the test disc are visual acuity tests, while those carried by the rotating dial are astigmatism tests. Other tests can also be carried out with such a device.

SUMMARY

According to the invention, the projection device is characterised in that the test disc and the test dial are both carried by the same plate, and in that this plate is mounted for rocking between two end positions, in one of which the test disc is in engagement with a drive means which is fixed in relation to the said plate and is driven by the motor associated with the test disc, the ring of the test disc which carries its test areas being then situated in the path of the light beam of the projection unit and the test dial being situated at a distance from the path of the said beam, while in the other end position the test dial is in engagement with the same drive means and is then situated in the path of the light beam of the projection unit, while the test disc is situated at a distance from the said path.

As the result of this arrangement a single motor is sufficient for the rotation of two test carrier elements, namely the test disc and the test dial, while the rotation of this disc can thus be effected in a controlled manner without requiring a separate motor.

In a second aspect of the invention, at least some of the test areas of the test disc comprise a plurality of generally radially arranged test lines, at least two of which correspond to different test scales.

This arrangement advantageously assists the arrangement on a single test disc of a large number of different tests belonging to various test scales, each of these test scales being selected by suitable selection of the light passage of the mask disc which is to be superimposed on the corresponding test areas of the test disc.

DESCRIPTION OF THE PREFERRED EMBODIMENT

In the embodiment illustrated in the drawings the test projection device of the invention comprises a casing 10 mounted for horizontal pivoting on an arm 11 carried by a base element (not shown), the casing 10 being locked in position on the arm 11 with the aid of a fastening button 12. The internal volume of the casing 10 is divided laterally into two compartments 10A, 10B, the first of which is formed between the front end wall 13 of the casing 10 and a first transverse plate 14 parallel to the wall 13, and the second between the plate 14 and a second plate 15 which in turn is parallel and fastened peripherally to the free edge of the casing 10.

The plate 14 is attached to the plate 15 by braces 16.

At the rear of the casing 10 a cover 17 is detachably fastened to the plate 15 and together with the latter forms a compartment 10C.

Figure 2:
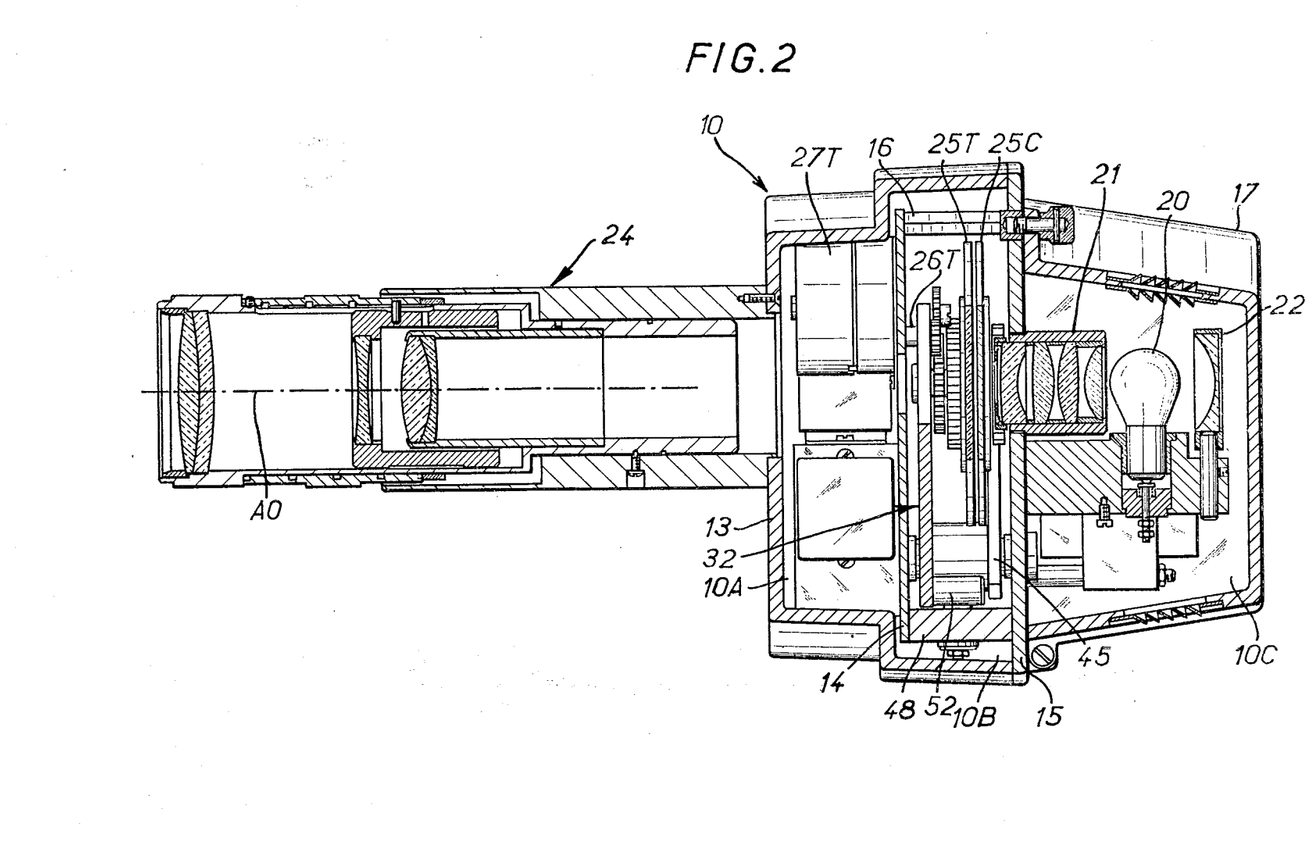
FIG. 2 is a view in longitudinal section of this device, passing through its optical projection axis.

Longitudinally the casing 10 and its cover 17 contain a light projection unit which in the usual manner (FIG. 2) comprises a projection lamp 20 disposed in the compartment 10C between a condenser 21 and a concentrating mirror 22, and an optical projection unit 24 of variable focal length which is carried by the casing 10, projecting from the end wall 13 of the latter.

A light projection unit of this kind is well known per se and will not be described in detail here.

The location of its optical axis is indicated by a broken line AO in the drawings.

In the compartment 10B of the casing 10 a first disc 25C, hereinafter referred to as the mask disc, is mounted for rotation.

Figure 3:
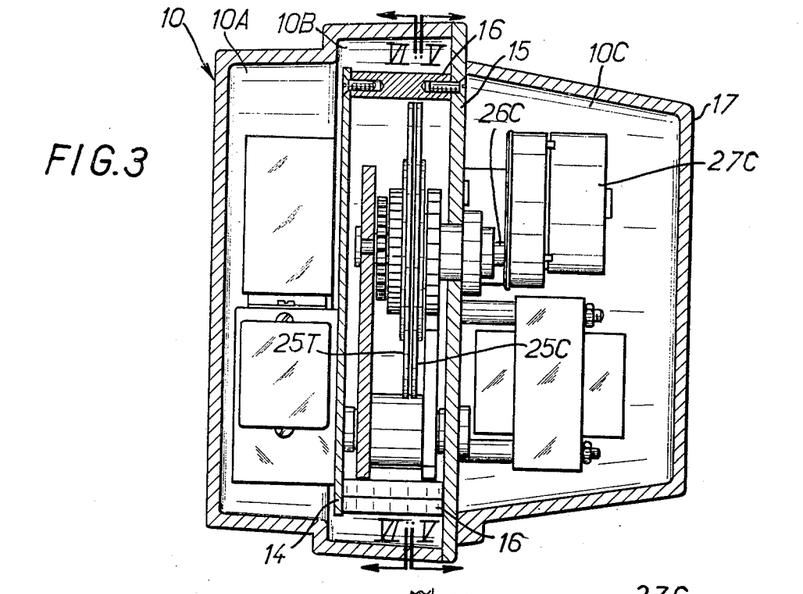
FIG. 3 is a view in longitudinal section of this device, passing through the geometrical axis of the mask disc which it contains.
Figure 4:
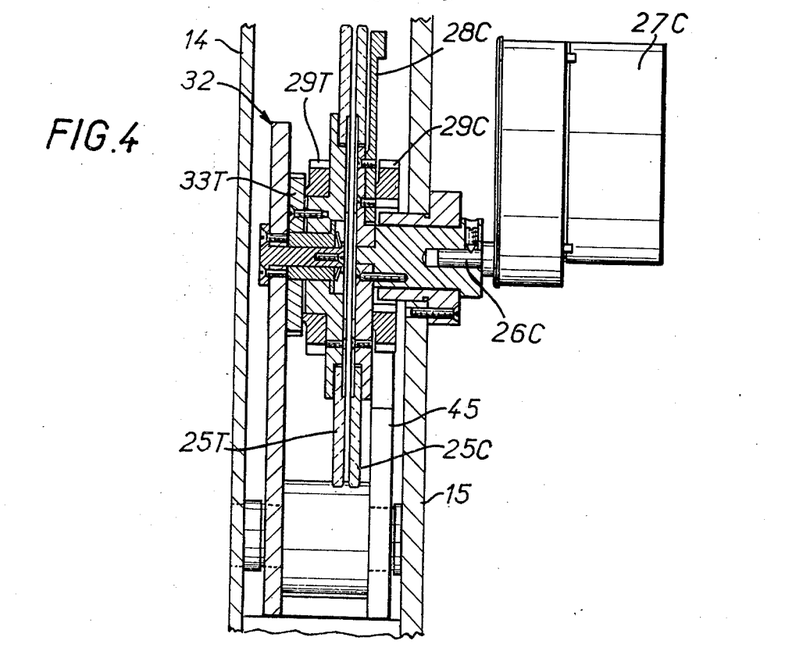
FIG. 4 shows on a larger scale a part of FIG. 3.
Figure 5:
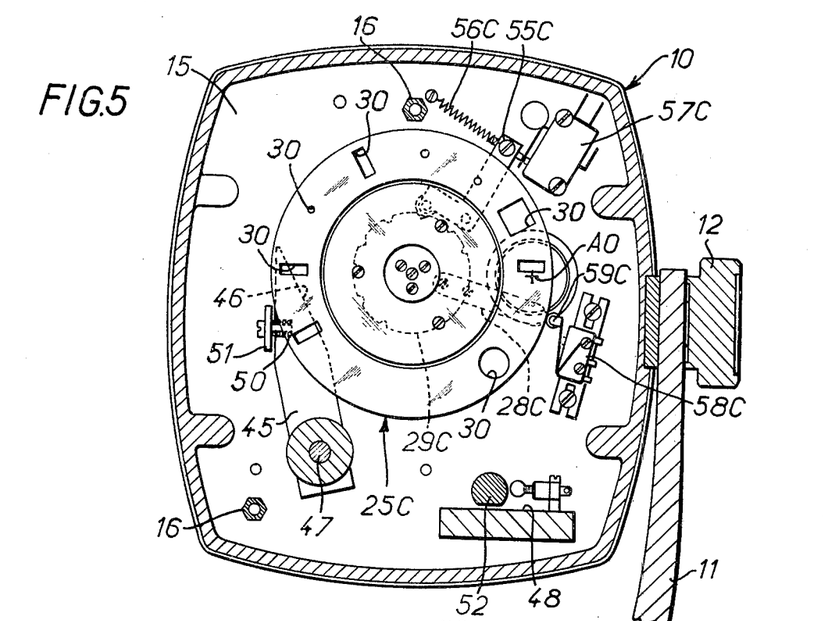
FIGS. 5 and 6 are cross-sectional views of the test projection device according to the invention, respectively on the lines V—V and VI—VI in FIG. 3.

This mask disc 25C is carried by the plate 15 and, as can be seen in FIGS. 3 and 4, is fastened on the output shaft 26C of a motor 27C accommodated in the compartment 10C formed by the cover 17.

On the mask disc 25C are angularly fastened on the one hand an arm 28C which extends substantially radially to a point close to the periphery of the mask disc 25C, and on the other hand a circular synchronisation cam 29C which is provided peripherally with teeth separated from each other by notches.

The arm 28C and the cam 29C, the duties of which will be indicated hereinbelow, are disposed between the disc 25C and the plate 15, FIG. 4.

Figure 1:
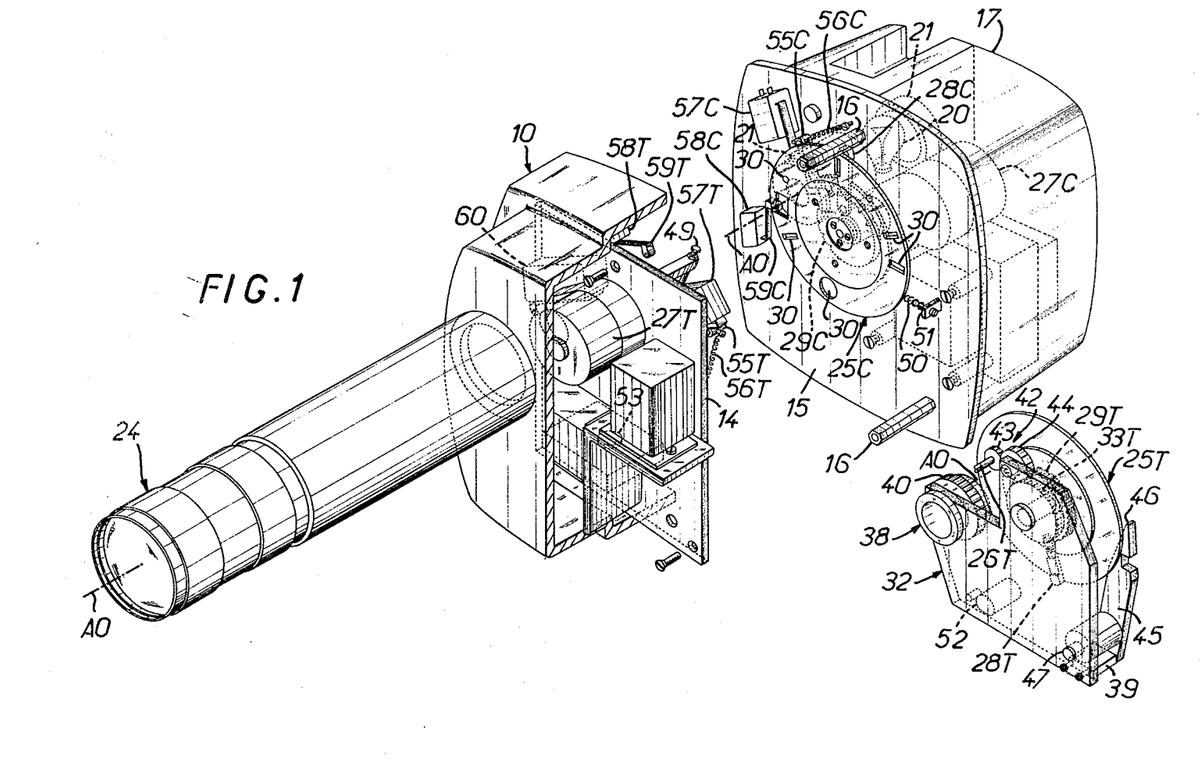
FIG. 1 is a partial view in exploded perspective, with parts broken away, of a test projection device according to the invention.

As can be seen in FIG. 1, the mask disc 25C is provided with a succession of apertures 30 distributed regularly in a circular arrangement on a ring comprised by the peripheral portion of disc 25C.

There are in particular a substantially square aperture, a number of radially elongated rectangular apertures, a circular aperture of large diameter, and a number of apertures of small diameter.

The ring of the mask disc 25C on which are situated the apertures 30 of the latter has a mean diameter substantially equal to the distance separating its axis of rotation from the optical axis AO of the projection unit described above, so that this ring is interposed in the light beam of this projection unit.

Between two apertures 30 the mask disc 25C is opaque; it consequently forms masks capable of masking the light beam of the projection unit with the exception of light passages formed by its apertures 30; in practice such apertures 30 may be formed by translucent or preferably transparent areas provided in an opaque ring.

The compartment 10B of the casing 10 contains a plate 32 which is parallel to the plates 14, 15 bounding this compartment.

This plate 32 is mounted for rocking on the plate 14, in the proximity of the latter, about a shaft 47 carried by the said plate 14 perpendicularly to its plane.

On this rocking plate 32 is mounted for rotation a second disc 25T, hereinafter referred to as the test disc.

On this test disc 25T are angularly fastened, as in the case of the mask disc 25C, on the one hand an arm 28T which extends substantially radially to a point close to the periphery of the test disc 25T, and on the other hand a circular synchronism cam 29T which is provided on its periphery with teeth separated two by two by notches.

A drive pinion 33T is in addition fastened on the test disc 25T.

The arm 28T, the synchronisation cam 29T, and the drive pinion 33T associated with the test disc 25T are disposed between the latter and the rocking plate 32 which carries them.

Figure 9:
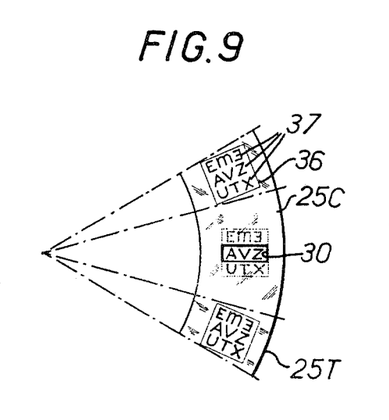
FIGS. 9 and 10 are diagrammatical elevational views of the test and mask discs of the test projection device of the invention, which illustrate the operation of the said device.

The test disc 25T carries circularly a succession of translucent test areas 36 which are distributed about a ring comprised by the peripheral portion of disc 25T and each of which carries radially one or more test lines 37, FIG. 9.

The mean diameter of the ring of the test disc 25T which carries the test areas 36 is substantially equal to the mean diameter of the ring of the mask disc 25C which carries the apertures 30 of the latter.

The rocking plate 32 also carries a circular dial 38 which carries tests and the inside diameter of which is substantially equal to the diameter of that of the apertures 30 of the mask disc 25C which is circular.

This test dial 38 is mounted for rotation on the rocking plate 32 and is fastened on a drive pinion 40 whose mid-plane in the examples illustrated is substantially the same as that of the drive pinion 33T of the test disc 25T.

In one aspect of the invention the same drive element 42, which is fixed in relation to the rocking plate 32, is conjointly associated with these drive pinions 33T and 40.

In the example illustrated this drive element 42 is carried by the plate 14 and comprises two pinions, namely a first pinion 43 fastened on the output shaft 26T of a motor 27T accommodated in the compartment 10A of the casing 10, and a second pinion 44 which meshes with the first pinion.

Parallel to itself the rocking plate 32 carries an arm 45 which is parallel thereto and whose innermost portion is interposed on the path swept by the arm 28C carried by the mask disc 25C and forms a rocking cam 46 for the said disc.

The rocking plate 32 is connected to its arm 45 by a brace 39, FIG. 1.

The rocking plate 32 is mounted for rocking between two end positions determined by stops 48, 49.

Figure 6:
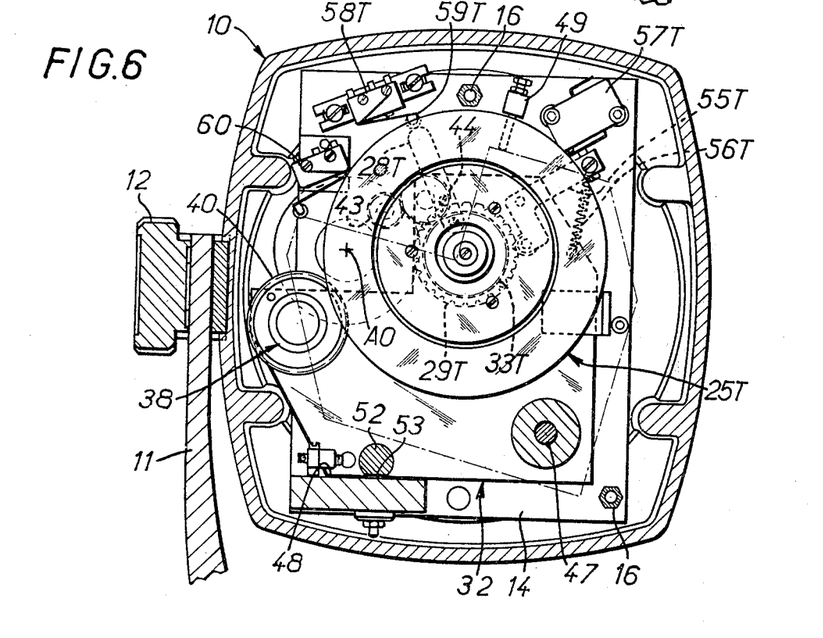

For the first of these end positions, which is determined by the stop 48 and which is shown in solid lines in FIG. 6, the test disc 25T is coaxial with the mask disc 25C, parallel to and at a short distance from the said mask disc 25C; conjointly, the drive pinion 33T of the test disc 25T is in mesh with the pinion 44 of the associated drive element 42.

Consequently, for this first position of the rocking plate 32 the test dial 38 is at a distance from the optical axis AO of the projection unit and its drive pinion 40 is at a distance from the associated drive element 42.

In a second end position of the rocking plate 32, which position is determined by the stop 49 and shown in broken lines in FIG. 6, the test dial 38 is interposed on the path of the light beam of the projection unit, the axis of rotation of this dial 38 then coinciding substantially with the optical axis AO of this projection unit, and conjointly its drive pinion 40 meshes with the pinion 43 of the associated drive element 42.

Figure 10:
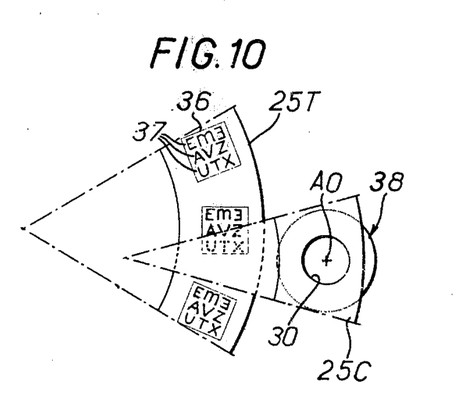

Consequently, in this second position of the rocking plate 32 the test disc 25T is offset in relation to the mask disc 25C and is moved entirely away from the light beam of the projection unit, FIG. 10.

The rocking of the rocking plate 32 takes place against the action of a return spring 50 interposed between, on the one hand, a bracket 51 fastened to the plate 15 and, on the other hand, the arm 45 carried by the rocking plate 32.

This return spring 50 urges the rocking plate 32 in the direction of the first of its end positions, in which the ring of the test disc 25T carrying the test areas of the latter is located on the path of the light beam of the projection unit.

At its bottom part the rocking plate 32 carries a stabilisation weight 52 which is of magnetic material and is intended to cooperate with a permanent magnet 53 carried by the stop 48, FIG. 6.

This stabilisation weight 52 is intended to lock the rocking plate 32 temporarily when it is in the first of its end positions.

With each of the synchronisation cams 29C, 29T associated respectively with the mask disc 25C and with the test disc 25T is associated a synchronisation lever 55C, 55T which by means of a spring 56C, 56T is brought back elastically into contact with the teeth of the corresponding synchronisation cam, these synchronisation levers respectively controlling synchronisation switches 57C and 57T.

The synchronisation microswitches 57C, 57T are interposed on the supply line of motors 27C, 27T in a manner which will be described later on; they are closed when the corresponding synchronisation levers 55C, 55T are in contact with the teeth of the corresponding synchronisation cams 29C, 29T, and are open when these levers 55C, 55T face the notches separating these teeth.

In addition, zeroising microswitches 58C, 58T are associated respectively with the mask disc 25C and the test disc 25T; these zeroising microswitches 58C, 58T are normally closed and their opening is controlled by levers 59C, 59T interposed respectively on the path of the arms 28C, 28T which are respectively fastened on the mask disc 25C and on the test disc 25T.

Another microswitch 60 is provided which is interposed on the path swept by the rocking plate 32 or by a finger fastened to the latter, during the rocking of the said plate.

Another microswitch 63, which is not shown in FIGS. 1 to 6, is likewise provided, this microswitch being normally closed and its opening being controlled by locking means associated with the rocking plate 32 in order to lock the latter in the first of its end positions described above, for example during transport.

These locking means may simply be composed of a rod engaged successively in the plate 15, in the rocking plate 32, and in the plate 14, this rod then being locked in this position and holding open the microswitch 63 (not shown in detail in the drawings).

Figure 7:
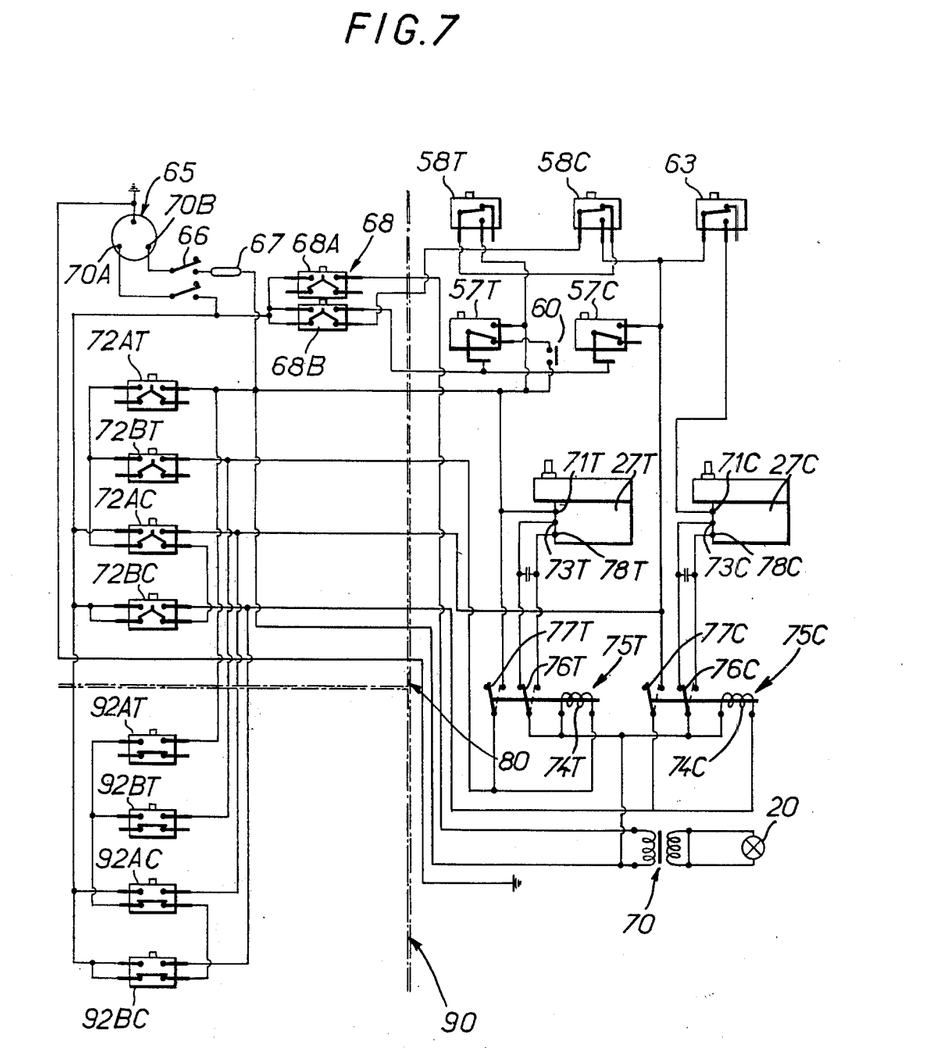
FIG. 7 is a block diagram of the electrical control of this test projection device.

The various microswitches 57C, 58C, 57T, 58T, 60 and 63 are grouped together in the block diagram shown in FIG. 7.

In this FIG. 7 can be seen at 27C the motor associated with the mask disc 25C, and at 27T the motor associated with the test disc 25T and with the test dial 38.

The projection lamp can also be seen at 20 in this Figure.

In FIG. 7, 65 designates any source of alternating voltage, for example the supply mains, 66 designates a mains switch, 67 a fuse, and 68 an on-off reversing switch adapted to be operated by two separate buttons, one corresponding to the "on" position and the other corresponding to the "off" position.

In the example illustrated the reversing switch 68 is in fact composed of two switches operated in parallel.

The first of these switches, which bears the reference 68A, applies voltage to the projection lamp 20 with the aid of a transformer 70.

The second of these switches, bearing the reference 68B, applies voltage in the "off" position, as shown in the Figure, to the zeroising microswitches 58C and 58T described above, and in the "on" position applies voltage to the synchronisation microswitches 57C and 57T described above, these various microswitches being disposed downstream of the reversing switch 68.

In the example illustrated voltage is applied to the zeroising microswitch 58T associated with the motor 27T with the aid of the zeroising microswitch 58C associated with the motor 27C, when the latter is open; the microswitch 58T is thus downstream of the microswitch 58C.

One of the terminals 70A of the source 65 is adapted to be connected to one of the terminals 71T of the motor 70T either by way of the corresponding synchronisation microswitch 57T or zeroising microswitch 58T, depending on the on-off position of the reversing switch 68, or, when the latter is in the "on" position, by way of one or the other of two push-button operated switches 72AT, 72BT corresponding respectively to the two directions of rotation of the motor 27T, these various microswitches being connected in parallel to the terminal 71T of the motor 27T.

The switch 72AT is connected direct to this terminal 71T, while the switch 72BT is connected to this terminal 71T by way of a reversing contact 77T controlled by a reversing relay 75T.

The application of voltage to the winding 74T of this reversing relay 75T is controlled by the second push-button switch 72BT, and this reversing relay 75T controls a second reversing contact 76T which brings the other terminal 70B of the source 65 into communication with one or the other of two terminals 73T, 78T of the motor 27T, thus permitting reversal of the direction of running of this motor, as will be described later on.

Similar arrangements are adopted for the motor 27C associated with the mask disc 25C, the supply of which is thus controlled by two push-button switches 72AC and 72BC in dependence on a reversing relay 75C having a winding 74C and a reversing contact 76C and 77T.

In the example illustrated the connection of the switches 72AT and 72BT associated with the motor 27T of the test disc 25T to the terminal 70A of the source 65 is effected by means of the switches 72AC, 72BC associated with the motor 27C of the mask disc 25C.

In the example illustrated the microswitch 60 controlled by the rocking plate 32 or by a finger fastened to the latter is connected downstream of the synchronisation switch 57T associated with the motor 27T, in series with the normally closed terminal of the contact controlled by the latter.

Furthermore, in the example illustrated the connection of the terminals 70A of the source 65 to the corresponding terminal 71C of the motor 27C — whether this connection is made by way of the microswitches 57C, 58C or 60, or by way of the reversing contact 77C controlled by the corresponding reversing relay 75C — is effected under the control of the microswitch 63 which, as described previously is controlled by a locking rod which, when necessary, effects the locking of the rocking plate 32 during transport.

Figure 8:
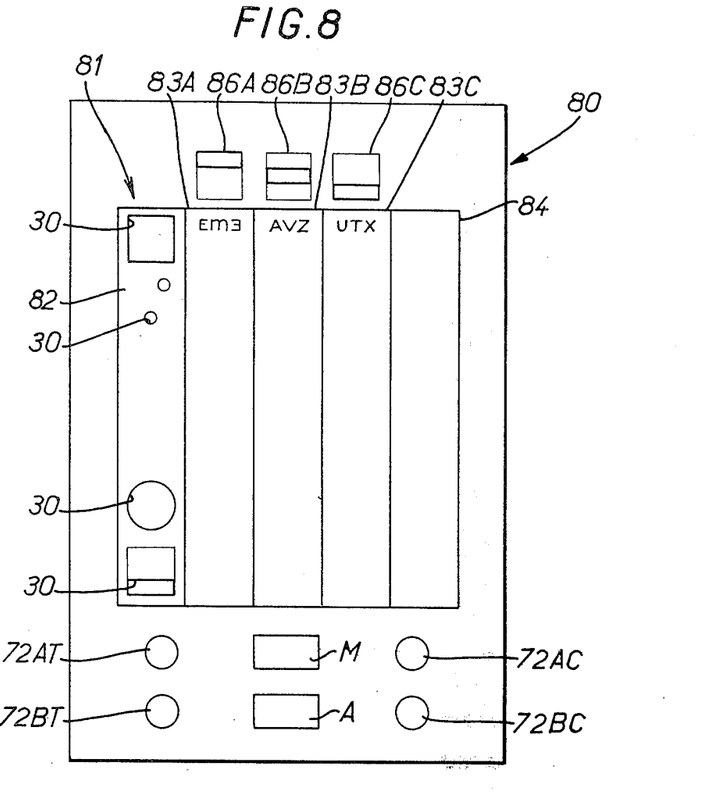
FIG. 8 is a plan view of the control keyboard of this device.

The push-button switches 72AT, 72BT, 72AC, 72BC and the on-off push buttons M, A controlling the reversing switch 68 are grouped together at the front on a control keyboard 80, FIG. 8.

The front of this control keyboard also contains a panel 81 having a first column 82 listing in succession the various openings 30 of the mask disc 25C, three columns 83A, 83B, 83C respectively listing the acuity tests of three different scales, for example a so-called E scale, a so-called Monoyer scale, and a so-called rational scale, and a column 84 successively listing various other types of tests, such as those relating to binocular vision, tests more particularly intended for children, and tests more particularly intended for amblyopic persons.

According to a special feature of the invention the test lines 37 of at least some of the translucent areas 36 of the test disc 25T each belong individually to the different acuity scales shown in the columns 83A, 83B, 83C.

Above these columns 83A, 83B, 83C are disposed symbols 86A, 86B, 86C indicating the nature of that particular aperture 30 of the mask disc 25C which must be superimposed on a translucent area 36 of the test disc 25T in order to isolate the test line 37 of that area which corresponds to the selected test scale.

In the example illustrated in FIG. 7, the keyboard 80 has associated with it a portable manipulator 90 comprising push-buttons 92AT, 92BT, 92AC, 92BC, which are respectively connected in parallel with the pushbutton switches 72AT, 72BT, and 72BC described above.

For reasons which will be indicated below the mask disc 25C and the test disc 25T are in a clearly determined angular position when at rest, the mask disc 25C being superimposed axially on the test disc 25T and having its drive pinion 33T in mesh with the pinion 44 of the associated drive element 42.

After the main switch 66 has been closed and the reversing switch 68 set to the "on" position, whereby the projection lamp 20 is lit, and after any acuity test scale has been selected, it is necessary to bring the mask disc 25C so that one of its rectangular apertures 30 which, corresponding to the test scale selected, are symbolised at 86A, 86B, or 86C, is brought into position on the path of the light beam of the projection unit of the apparatus.

In order to do this, it is necessary to depress one or the other of the switches 72AC, 72BC, or one or the other of the switches 92AC, 92BC which duplicate them.

When, for example, the switch 72AC is operated, this applies voltage at least temporarily to the motor 27C by way of the microswitch 63C, the latter being assumed to be closed and the rocking plate 32 consequently being assumed to be unlocked and free to pivot.

As soon as the motor 27C starts to turn it closes the associated synchronisation microswitch 57C, so that even if the action on the switch 72AC is short-lived the rotation of the motor 27C and consequently that of the mask disc 25C operated by it continue.

This rotation continues until the corresponding synchronisation lever 55C drops into the first notch encountered on the synchronisation cam 29C so that the synchronisation lever 55C frees the microswitch 57C; the latter thereupon returns to its open position.

This return of the microswitch 57C to the open position stops the rotation of the motor 27C, and this rotation can be resumed only in response to the re-operation of the switch 72AT.

The disc 25C thus advances step by step under the control of the synchronisation cam 29C, provided that the switch 72AT is operated a number of times in succession, each of these operations corresponding to a rotation of the disc 25C by one step.

Action on the switch 72BC or on the switch 92BC duplicating it would obviously similarly advance the disc 25C step by step, but in the opposite direction of rotation from that previously occurring, the winding 74C of the associated reversing relay 75C then being under voltage and causing the reversing contacts 76T, 77T controlled by it to change position.

Similarly, after selection of the aperture 30 corresponding to the selected test scale, a series of actions on the switches 72AT, 72BT, or 92AT, 92BT effects the step-by-step rotation of the test disc 25T, in one direction or the other depending on which of the switches 72AT, 72BT, or 92AT, 92BT is operated.

For each step of the test disc 25T one of the translucent areas 36 of the latter is superimposed on the aperture 30 of the mask disc 25C in the light beam of the projection unit of the apparatus, and this aperture 30 is located opposite the test line 37 of the area 36 corresponding to the test scale selected in conjunction with this aperture 30.

In the usual manner the step-by-step advance of the test disc 25T corresponds to increasing or decreasing presentation of the test lines of the scale selected.

By acting once more on the switches controlling the step-by-step rotation of the mask disc 25C it is possible for each of these test lines to select all or part of the line.

It will be observed that since the switches 72AT and 72BT are in series with the switches 72AC, 72BC and since these switches 72AC, 72BC are reversing switches, the rotation of the test disc 25T is impossible during the rotation of the mask disc.

In order to utilise the test dial 38 it is sufficient to act on the switches controlling the mask disc 25C so as to bring into the light beam of the projection unit of the apparatus that one of the apertures 30 of the said mask disc 25C which is circular.

Upon the corresponding rotation of the mask disc 25C the arm 28C carried by the latter comes into contact with the cam 46 formed by the face of the arm 45 fastened to the rocking plate 32, so that the said plate is rocked from the first of its end positions, which it occupied previously, to the second end position described above.

As described above, in this second end position the pinion 40 which is fastened on the test dial 38 is in mesh with the pinion 43 of the drive element 42, while the drive pinion 37T of the test disc 25T is disengaged from the pinion 44 of this drive element 42 and the test disc 25T is moved completely away from the projection light beam (FIG. 10), the dial 38 taking the place of the test disc 25T in this respect.

Shortly before the rocking plate 32 arrives at this second position the finger 62 carried by the arm 45 which is fastened to the said plate has temporarily closed the microswitch 60, thereby effecting a brief rotation of the motor 27T in such a manner that through the resulting rotation of the pinion 43 of the drive element 42 the engagement of the drive pinion 40 of the dial 38 with the said pinion 43 is facilitated.

When the test dial 38, and only this dial, is thus interposed on the light beam of the projection unit, any action on the switches 72AT, 72BT, or 92AT, 92BT causes it to rotate continuously in one direction or the other.

Further action on the switches controlling the step-by-step rotation of the mask disc 25C brings the arm 28C of the latter away from the cam surface 46 of the arm 45 of the rocking plate 32, and the latter thereupon returns to the first of its end positions through the action of its return spring 49.

When the reversing switch 68 passes into the "off" position it applies voltages to the microswitches 58C, 58T, as mentioned above, and the latter, similarly to the microswitches 57C, 57T, supply current to the corresponding motors 27C, 27T until the arms 28C, 28T fastened to the mask disc 25C and test disc 25T act on the microswitches 58C, 58T, and thus interrupt the rotation of these discs.

Consequently the position of these discs when at rest is accurately determined angularly.

In the example described, since the microswitch 58T is downstream of the microswitch 58C in relation to the source 65, the zeroising of these discs is effected first for the mask disc 25C and then for the test disc 25T. As will have been understood, the microswitch 63 makes it possible to prevent the burning-out of the motor 27C if the switches 72AC, 72BC, or 92Ac, 92BC are operated when the rocking plate 32 is locked by the locking means associated with it.

The present invention is obviously not limited to the embodiments described and illustrated but includes any alternative embodiment within the scope of the appended claims.

In particular, in a variant which is not illustrated the mechanical synchronisation means which are associated with a disc, and which comprise the synchronisation cam fastened on the disc and the microswitch operated by it for the purpose of controlling the corresponding motor, may be replaced by electronic synchronisation means comprising position markings on one face of a disc of this kind, for example reflecting markings, in cooperation with an electro-optical position detector which is adapted to scan these markings and which controls the supply of current to the said motor.

Action on the appropriate push-button of the control keyboard or of the portable manipulator associated with the latter effects the starting-up of the corresponding motor in the forward or reverse direction, and this motor is automatically stopped when the corresponding position detector has scanned a position marking on the disc in question, unless the action on the said push-button is continued or repeated.

This disc thus advances step by step, as previously.

Similar arrangements can be adopted for returning a disc to zero and/or for rocking the plate carrying the test disc.

The signals transmitted by the various detectors are preferably processed by a central control logic system, which regroups the advance control information to be applied to the motors, supervises the return of the discs to zero in such a manner that this return to zero is effected first for one disc and then for the other, and supervises the different phases of rocking of the plate carrying the test disc.

The construction of a central control logic system of this kind is within the scope of those skilled in the art, once the functions which it has to perform have been defined, as indicated above.

I claim:

1. A device for projecting images such as tests for eyesight examination onto a screen, comprising a casing, a light projection unit mounted on said casing for projecting a light beam, a rocking plate rockably mounted on said casing between two end positions relative to the light beam, a test disc including a ring having a plurality of translucent test areas and a test dial also carrying at least one test area, said test disc and said test dial being both mounted for rotation on and relative to said plate, said test disc being in the path of the light beam in said first end position of said plate and the axis of rotation of said test dial substantially coinciding with the axis of the light beam in said second end position of said plate, a mask disc including a ring having a plurality of light passages mounted for rotation in said casing and disposed along the path of the light beam axially spaced from said rocking plate, said light passages on said mask disc being individually superpositionable on at least some of the test areas of said test disc in said first position, a separate motor for rotating each of said discs about its axis of rotation, drive means fixed relative to said rocking plate and driven by the motor associated with said test disc, said drive being in operative engagement with said disc to rotate said test disc when said rocking plate is in said first position and in operative engagement with said test dial to rotate said test dial when said plate is in said second position.

2. A device according to claim 1, wherein the drive means comprises a gear train fixed for rotation with the output shaft of the motor associated with the test disc, the test disc and the test dial both being mounted for rotation with a drive pinion adapted to engage one of the gears of gear train.

3. A device according to claim 1, wherein said rocking plate is fastened to a rocking cam, said rocking cam being interposed in the path of movement of an arm mounted for rotation with the mask disc for rocking said rocking plate.

4. A device according to claim 1, wherein said rocking plate is mounted for rocking movement against the action of a return spring.

5. A device according to claim 4, wherein said return spring urges said rocking plate towards said first end position.

6. A device according to claim 1, wherein said rocking plate carries a stabilizing weight of magnetic material, and wherein said rocking plate stabilizing weight faces a fixed permanent magnet, in at least one of said end positions of said plate to temporarily lock said plate in that position.

7. A device according to claim 1, wherein when the test disc is in engagement with said drive means, it is coaxial with the mask disc.

8. A device according to claim 1, wherein an electrical contact is located in the proximity of one of said end positions of said rocking plate, said electrical contact being in an electrical circuit supplying said motor associated with the test disc, said motor being supplied by brief contact every time said rocking plate comes close to said one end position.

9. A device according to claim 1, wherein locking means are associated with said rocking plate for locking the latter in one of said end positions, and said locking means actuating an electrical contact disposed in an electrical supply circuit supplying said motor associated with the mask disc.

10. A device according to claim 1, wherein a synchronizing cam is associated with each of the test disc and mask disc, each synchronizing cam being fixed for rotation with its associated disc and having teeth separated by notches for controlling a synchronizing microswitch disposed in the electrical supply circuit for the motor of its associated disc for the step-by-step rotation of the disc, each said microswitch being closed by one of the teeth of the synchronizing cam and opened by a notch thereof.

11. A device according to claim 10, wherein each of the test disc and the mask disc has an arm fixed for rotation therewith for controlling a zerozing microswitch in the electrical supply circuit of its associated motor when the device is in the "off" position, each said zeroizing microswitch being normally closed the opening thereof being controlled by its arm.

12. A device according to claim 11, wherein the zeroizing microswitch associated with the test disc is downstream of the zeroizing microswitch associated with the mask disc relative to the electrical supply source.

13. A device according to claim 11, wherein the synchronizing microswitch and the zeroizing microswitch associated with each said disc are connected in parallel, and an on-off throw-over switch disposed between a power source for said last mentioned micro switches and said last-mentioned microswitches, said on-off throw-over switch supplying its synchronizing microswitch in the "on" position and supplying the zeroizing microswitch in the "off" position.

14. A device according to claim 1, wherein said rocking plate is fastened to a rocking cam interposed in the path of an arm mounted for rotation with the mask disc for effecting the rocking movement of the said rocking plate, said arm being associated with the mask disc for controlling a zeroizing microswitch in the electrical supply circuit of the motor associated with the mask disc when the device is in the "off" position, each said zeroizing microswitch being normally closed, the opening thereof being controlled by the associated arm.

15. A device according to claim 1 further comprising a control board including a plurality of control switches for the device, and on a face thereof a column listing the light passages of the mask disc, and a plurality of test columns listing the possible tests in accordance with various test scales.

16. A device according to claim 15, wherein at least some of the test areas on the test disc comprise a plurality of test lines at different test scales.

17. A device according to claim 16, wherein each of the test columns on the face of the control board is accompanied by a symbol indicating the nature of the light passage of the mask disc which is to be superimposed on a said test area of the test disc in order to isolate a said test line which corresponds to the test scale of the test column.

18. A device according to claim 1, wherein synchronizing means is associated with each of the test disc and the mask disc, including position markings on a face of the associated disc in conjunction with an electro-optical position detector which is adapted to scan said markings, said detector also controlling current supply to the motor associated with the disc.

* * * * *